(12) United States Patent
Griffith et al.

(10) Patent No.: US 6,178,353 B1
(45) Date of Patent: Jan. 23, 2001

(54) LAMINATED MAGNET KEEPER FOR IMPLANT DEVICE

(75) Inventors: Glen A. Griffith, Newbury Park; Richard P. Malmgren, Castaic, both of CA (US)

(73) Assignee: Advanced Bionics Corporation, Sylmar, CA (US)

( * ) Notice: Under 35 U.S.C. 154(b), the term of this patent shall be extended for 0 days.

(21) Appl. No.: 09/353,236

(22) Filed: Jul. 14, 1999

Related U.S. Application Data

(60) Provisional application No. 60/094,300, filed on Jul. 27, 1998.

(51) Int. Cl.[7] .................................................. A61N 1/378
(52) U.S. Cl. ............................................................ 607/61
(58) Field of Search ................................ 607/33, 61, 57, 607/55, 56

(56) References Cited

U.S. PATENT DOCUMENTS 5,690,693 * 11/1997 Wang et al. ............................ 607/61
6,067,474 * 5/2000 Schulman et al. ...................... 607/57

* cited by examiner

Primary Examiner—Scott M. Getzow
(74) Attorney, Agent, or Firm—Bryant R. Gold

(57) ABSTRACT

An implantable medical device, such as an implantable cochlear stimulator (ICS) system, utilizes laminated, sectionalized or particle-ized permanent magnets and/or keepers in both the implant portion and external (non-implanted) portion so as to reduce the electrical energy absorbed by both the implant device and the external device when in use. In one embodiment, the implant device employs a sectionalized, laminated or particle-based "keeper", while the external device employs a sectionalized, laminated or particle-ized magnet, making the implant device immune to being damaged by MRI (magnetic resonance imaging). The combination of the sectionalized/laminated/particle magnets and the sectionalized/laminated/particle keepers creates a very high electrical resistance path across the boundaries of the laminations, sections, or particles, thereby reducing the magnitude of eddy currents that would otherwise flow transversely through the keeper in the presence of a magnetic flux passing through the keeper or magnet. The reduction of eddy currents, in turn, reduces energy loss.

20 Claims, 5 Drawing Sheets

LAMINATED MAGNET KEEPER FOR IMPLANT DEVICE

This application claims the benefit of U.S. Provisional Patent Application Ser. No. 60/094,300, filed Jul. 27, 1998.

BACKGROUND OF THE INVENTION

The present invention relates to implantable devices, and more particularly to implantable medical devices having a permanent magnet therein that aligns an external (non-implanted) coupling device with the implantable device so that an electromagnetic signal may be optimally coupled between the two devices.

It is known in the art for an implantable medical device, e.g., implantable cochlear stimulator (ICS), to have a permanent magnet placed therein. An external (non-implanted) device, e.g., a headpiece of an ICS system, also has a permanent magnet placed therein. Both the external device and the implantable device may have coils mounted therein to allow power and information to be electromagnetically coupled, e.g., inductively coupled, between the two devices. Optimum signal and power coupling occurs when the implanted coil in the implantable device and the external coil in the external device are properly aligned. The magnetic attraction between the two permanent magnets, one located in the implantable device (typically in the center of the implant coil) and the other located in the external device (also typically located in the center of the external coil), magnetically hold the external device in a proper position so that the needed alignment between the two devices is maintained. See, e.g., U.S. Pat. Nos. 4,352,960 (Dormer et al.) and 4,726,378 (Kaplan), both of which patents are incorporated herein by reference.

It is also known in the art to replace one of the magnets, e.g., the magnet in the implant device, with a "keeper". A keeper is generally made from a material which is not magnetic, per se, i.e., is not magnetized, but which provides a low reluctance magnetic path for magnetic flux. The use of a keeper advantageously improves the resistance of the implant system to MRI magnetic fields, in the event such MRI fields should be applied to the patient. That is, should MRI (magnetic resonance imaging) be conducted on the patient having the implant, the magnet in the implant becomes demagnetized and distorts the MRI image. A keeper, if used in place of the implant magnet, is not damaged by the MRI and distorts the MRI image less.

Disadvantageously, when power and signals must be electromagnetically transferred between the implant device and the external device, placing a magnet or keeper within the coils used for the power and signal transmission absorbs power and reduces the efficiency of the system. Here, system efficiency is defined as the ratio of input power delivered to a transmission coil input to output power recoverable at a receiving coil. What is needed, therefore, is a system that allows magnetic attraction to maintain a proper alignment between an implantable device and an external device without having the magnetic elements absorb large amounts of power, thereby making the system more efficient. What is further needed is such a system that is compatible with MRI, i.e., that allows MRI to be conducted when necessary without harming the implant device and without significantly distorting the MRI image.

SUMMARY OF THE INVENTION

The present invention addresses the above and other needs by laminating and/or sectionalizing the magnet and/or keeper used in both the implant device and external device so as to reduce the electrical energy absorbed by both the implant device and the external device. In order to avoid being damaged by MRI, it is preferred that the implant device employ a sectionalized or laminated "keeper", while the external device employ a laminated or sectionalized magnet, or a magnet comprising small electrically-isolated magnetic particles. The use of such laminated, sectionalized or particle-ized components advantageously creates a very high electrical resistance path across the boundaries of the laminations, sections, or paticles, thereby reducing the magnitude of eddy currents that would otherwise flow transversely through the keeper in the presence of a magnetic flux passing through the keeper or magnet. The reduction of eddy currents, in turn, reduces energy loss.

In accordance with one aspect of the invention, an implantable medical device includes a receiving coil adapted to be electromagnetically coupled with a transmitting coil of an external device, and a magnetic element responsive to a magnetic field. The magnetic element holds the implantable medical device in a desired position that aligns the receiving coil with the transmitting coil for efficient power and signal transfer between the receiving and transmitting coils. Also included are means for reducing energy loss within the magnetic element as power and signal transfers occur between the receiving and transmitting coils. Thus, the implantable medical device operates with less loss relative to the amount of energy coupled into the receiving coil.

In accordance with another aspect of the invention, a medical device system is provided that includes an implantable part and an external (non-implanted) part. The implantable part and the external part each have a coil therein through which power may be inductively coupled from the external part to the implantable part when the respective coils are aligned. The system includes a first magnetic element in the external part, and a second magnetic element in the implanted part adapted to be magnetically attracted to the magnetic element in the external part. This magnetic attraction aligns the respective coils for efficient power and signal transfer. Moreover, as a key element of the system, at least the second magnetic element has electrical resistance blocking means therein for minimizing the formation and/or flow of eddy currents in the second magnetic element when in the presence of a magnetic field. Thus, with eddy currents minimized or eliminated, the transfer of power into the implantable part may be made more efficient.

In accordance with yet a further aspect of the invention, there is provided a method for reducing power losses associated with the transfer of energy into an implantable medical device from an external device via inductive coupling. For such method, it is understood that the implantable medical device has a first magnetic element therein adapted to be magnetically attracted to a second (non-implanted) magnetic element. The method includes the steps of: (1) positioning the first magnetic element relative to an implanted coil within the implantable medical device so that when the first magnetic element is maximally magnetically attracted to the second magnetic element, the implanted coil is aligned with an external coil for efficient inductive coupling; and (2) configuring the first (implanted) magnetic element so as to minimize the formation of eddy currents therein when the second magnetic element is in the presence of a magnetic field.

It is thus an object of the present invention to provide an ICS system that efficiently transfers signals and power between an external portion and an implanted portion.

It is another object of the present invention to provide an implant device that reduces the amount of energy lost to the magnet or keeper, thereby increasing the efficiency of the implant device.

It is a further object of the invention to provide an implantable cochlear stimulator (ICS) system having sectionalized, laminated, or particle-ized magnets and/or keepers in an external portion and in an implantable portion, which magnets and/or keepers are used to hold the external portion in proper alignment with the implant portion when the ICS system is in use, and wherein the sectionalized or laminated magnets and/or keepers, or other magnetic elements made from small electrically-isolated magnetic particles, reduce the amount of energy lost in the magnets or keepers, thereby making energy transfer between the two components more efficient.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
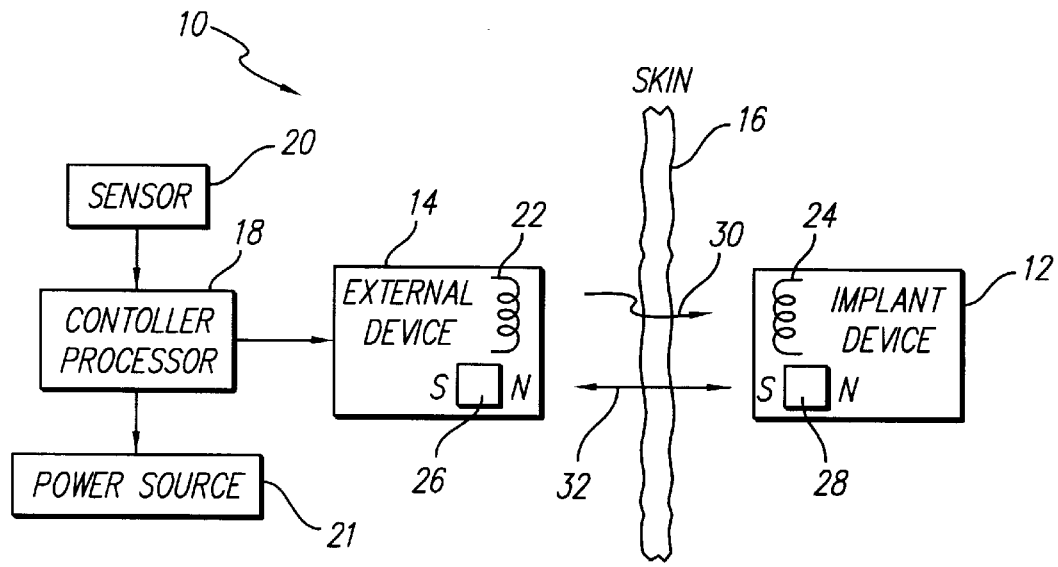
FIG. 1 is a block diagram of an implantable medical system, such as an implantable cochlear stimulation (ICS) system.

Referring first to FIG. 1, there is shown a simplified block diagram of an implantable medical system 10. As seen in FIG. 1, the system 10 includes an implant device 12 and an external device 14. The implant device 12 is implanted, i.e., located subcutaneous, or underneath the skin 16 of a patient. The external device 14 is located external to the patient, i.e., is not implanted within the patient, although typically the external device 14 will be located adjacent the skin 16 of the patient, and may be worn next to the skin 16 of the patient on a continual or part-time basis.

The external device 14 is also typically coupled electrically to a controller/processor 18, which controller/processor 18 may also be worn or carried by the patient. One or more sensors 20 is typically connected to the controller/processor 18 in order to provide the controller/processor 18 with sensed information that determines, in part, the type of control signals that the controller/processor 18 sends to the external device 14 for communication to the implant device 12. A suitable power source 21, e.g., a battery, provides operating power for the entire system 10.

The external device 14 is electrically coupled to the implant device 12 through the use of an external coil 22 (located within the external device 14) and an implant coil 24 (located within the implant device 12). It should be noted that the implant coil 24 may also be referred to as a receiving coil 24, and the external coil 22 may be referred to as the transmission coil 22, inasmuch as the coil 22 transmits power and/or control information (represented by the wavy arrow 30 in FIG. 1) that are received by the coil 24. For simplicity, FIG. 1 shows power/signals 30 being sent only from the external device 14 to the implant device 12. However, it is to be understood that signals may also be sent (transmitted) from the implant device 12 to the external device 14.

The medical system 10 shown in FIG. 1 is intended to generically apply to many different types of medical systems, e.g., tissue or nerve stimulators, implantable sensors or monitors, and the like.

A preferred medical system 10 for purposes of the present invention is an implantable cochlear stimulator (ICS) system. In such ICS system, the implant device comprises an ICS (12), and includes an electrode array (not shown) that is intended to be implanted within the cochlea of the patient. The implant coil 24, and related electrical circuitry, and then implanted in a convenient location, e.g., behind the ear of the patient. Further in such system, the external device comprises a headpiece (14) intended to be magnetically attracted to and held in position on the outside of the patient's skin, adjacent the ICS. The headpiece (14) is then connected to a speech processor (18), and the speech processor in turn is coupled to a microphone (20).

In operation, the microphone (20) senses audible sounds, which are conveyed to the speech processor (18). Note, in some embodiments, the processor (18) and microphone (20) may be included within the same housing as the headpiece (14). The speech processor (18) then processes the sensed sounds, and sends appropriate electrical control signals to the headpiece (14) for transmission as control/power signals (30) to the receiving coil (24) of the ICS (12). The ICS (12) derives its operating power from the signals (30) thus received, and further receives control information from the signals (30) thus received. This control information indicates which electrodes of its electrode array should provide an electrical stimulus to the cochlea, and the amplitude of such stimulus. In this manner, then, the nerves in the cochlea of a deaf patient are provided with a pattern of electrical stimuli representative of sounds sensed through the microphone (20), thus affording the patient the sensation of "hearing".

As explained more fully below, in order to achieve an optimum signal and power transfer between the implant coil 24 and the external coil 22, it is necessary that the coils 22 and 24 be properly aligned with each other. Such alignment has typically been achieved by including a first magnet 26 in the external device and a second magnet 28 in the implant device. In some instances, the second magnet 28 may be replaced with a magnetic element, i.e., a magnet keeper, or an element that is not a magnet, but rather is an element that creates a low reluctance path for magnetic flux, and which is thereby strongly attracted to the first magnet 26. The use of a magnetic keeper may be desirable, for example, if the patient perceives that there may someday be a need to be subjected to magnetic resonance imaging (MRI). MRI and implanted magnets are not compatible with each other inasmuch as the presence of the implanted magnet could interfere with the MRI process. Moreover, the strong magnetic fields associated with MRI could damage an implanted magnet.

Regardless of whether the implanted magnetic element 28 is a magnet or a magnetic keeper, the magnetic attraction between the two magnetic elements 26 and 28, represented in FIG. 1 by the arrow 32, not only serves to properly align the two coils 22 and 24 so that optimum signal/power transfer can occur, but also provides a holding force that maintains the external device 14 in its desired position adjacent the skin 16 of the patient. In the case of an ICS system, for example, the magnetic attraction serves to hold the headpiece (14) behind the ear of the patient, in proper alignment with the implanted ICS (12).

The presence of the magnet elements 26 and 28, in close proximity to the coils 22 and 24, which close proximity is required in order to maintain the desired alignment between the coils, disadvantageously also degrades the transfer of power to the implant device. This is because some of the power transmitted from the external device is lost within the magnet elements 26 and 28, as explained more fully below. The present invention is directed to particular designs and configurations for the magnetic elements 26 and 28 that minimize the power losses that occur in such elements. By minimizing such losses, the operating efficiency of the system 10 may advantageously be improved, thereby allowing, e.g., a longer operating time between battery recharges, or a smaller battery (power source 21) to be used.

Figure 2:
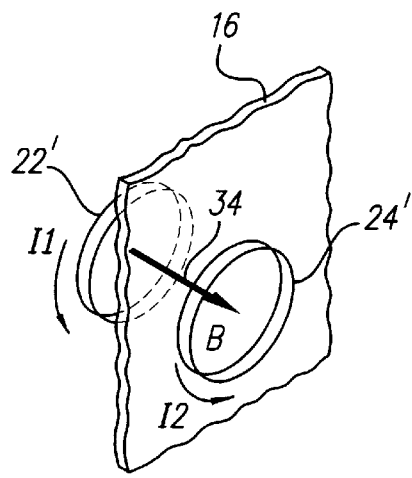
FIG. 2 illustrates the proper alignment between two coils in order to achieve optimum inductive coupling between the coils when one of the coils is spaced apart from the other.

To better understand and appreciate why losses occur with the magnetic elements 26 and 28 when in the presence of a magnetic field, reference is made to FIGS. 2 and 3. FIG. 2 illustrates the proper alignment between two coils 22' and 24' in order to achieve optimum coupling between the coils when one of the coils, e.g., coil 24', is spaced apart from the other coil 22', by at least the thickness of the skin 16. It is a well known principle of physics that when an electrical current I1 flows within a coil 22', a magnetic field B, represented by the arrow 34 in FIG. 2, is created. By convention, the magnetic field B has a magnitude and direction associated with it, with the arrow 34 pointing in the direction of the north pole associated with the magnetic field B. It is helpful to think of a magnetic field B as having magnetic flux associated therewith, which magnetic flux flows out from the magnet in the direction of the magnetic's north pole, spreads out and returns to the magnet at the magnet's south pole.

If the magnetic flux created by the current I1 in coil 22' varies as a function of time, i.e., if the current I1 is an ac current as opposed to a dc current, it also induces a current I2 in a coil 24' that is aligned with the coil 22'. The magnitude of the current I2 induced in coil 24' by the varying magnetic flux created by current I1 is a function of how much of the magnetic flux created by current I1 flowing in coil 22' passes through coil 24'. A maximum current I2 is induced in coil 24' when a maximum amount of varying magnetic flux passes through coil 24'. Such maximum current I2 occurs when the coil 24' is properly aligned with the coil 22'. The best alignment between two coils occurs when the distance separating the coils is minimized, and the centers of the coils are coaxial.

When two coils are aligned such that an ac signal (electrical current I1) applied to one induces an ac signal (electrical current I2) in the other, the coils are said to be "inductively coupled" with each other. It is noted that inductive coupling is the principle upon which many electromagnetic components operate, e.g., transformers. That is, as is known in the art, a transformer is used to transfer power from one circuit, connected to one of the coils, to another circuit, connected to the other coil, without a direct electrical connection between the coils or circuits. Through proper design control, e.g., selecting the number of turns in the coils, spacing between coils, etc., it is possible to achieve a desired signal transformation as the signal is transferred from one circuit to the other.

Inductive coupling is typically the principle used to transfer power from an external device 14 to an implant device 12, e.g., an ICS. That is, a carrier signal having a selected frequency F1, is applied to coil 22', so as to cause an ac current I1 to flow through the windings of the coil 22'. The flow of current I1 causes a corresponding alternating magnetic field to be created, which alternating magnetic field also passes through coil 24' and induces an ac current I2 in the coil 24'. The frequency of the current I2 is the same as the frequency of the current I1.

Through appropriate electrical circuitry, e.g., a rectifier circuit, the power associated with the current I2 may be recovered and used to power the implant device 12. Control signals may also be transferred from the external device 14 to the implant device 12 by modulating the amplitude of the current I1 with a modulated control signal at a frequency F2, where F2 is typically much less than the frequency F1. Such modulated signal may then be recovered from the current I2, induced on the implant coil 24', using conventional demodulation techniques.

Figure 3A:
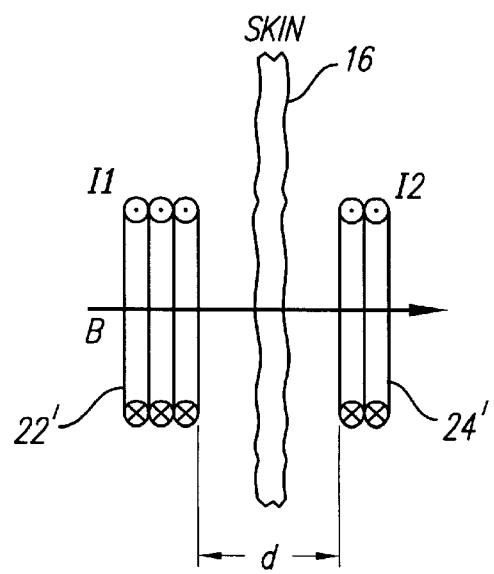
FIG. 3A schematically illustrates all implanted coil aligned with an external coil in order to achieve optimum power transfer between the two coils.

FIG. 3A schematically illustrates the desired alignment between the implanted coil 24' and the external coil 22'. Each coil is shown in cross section with a dot within a circle, i.e., the symbol "⊙", signifying an electrical current that is flowing out of the plane of the paper, and with an "x" within a circle, i.e., the symbol "⊗", signifying an electrical current that is flowing into the plane of the paper. Such are conventional symbols used in the electrical arts. Thus, as shown in FIG. 3A, the current I1 and the current I2, at a given instant of time, are flowing out of the plane of the paper at the top of the coil, and are flowing into the plane of the paper at the bottom of the coil. The current I1 flowing in this direction creates the magnetic field B having the polarity (direction) shown, which in turn induces the current I2 flowing in the direction shown. These directions change or alternate, as the direction of flow of current I1 changes.

The proper alignment between coils 22' and 24' is achieved when as much of the magnetic flux as possible associated with the magnetic field B (created in the external coil 22') passes through the implanted coil 24'. Where there is a non-zero lateral separation distance "d" between the two coils, it is not possible for all of the magnetic flux created in coil 22' to pass through coil 24'. However, by aligning the centers of the coils so that each is co-axial with the other, and by keeping the distance "d" as small as possible, it is possible for much of the magnetic flux created in coil 22' to also pass through coil 241, thereby providing efficient inductive coupling between the two coils.

For illustrative purposes only, the implanted coil 24' is depicted in FIG. 3A as having just two turns, while the external coil 22' is depicted as having three turns. The number of turns used in each of the implanted and external coils will vary, of course, depending upon the particular application and design.

Figure 3B:
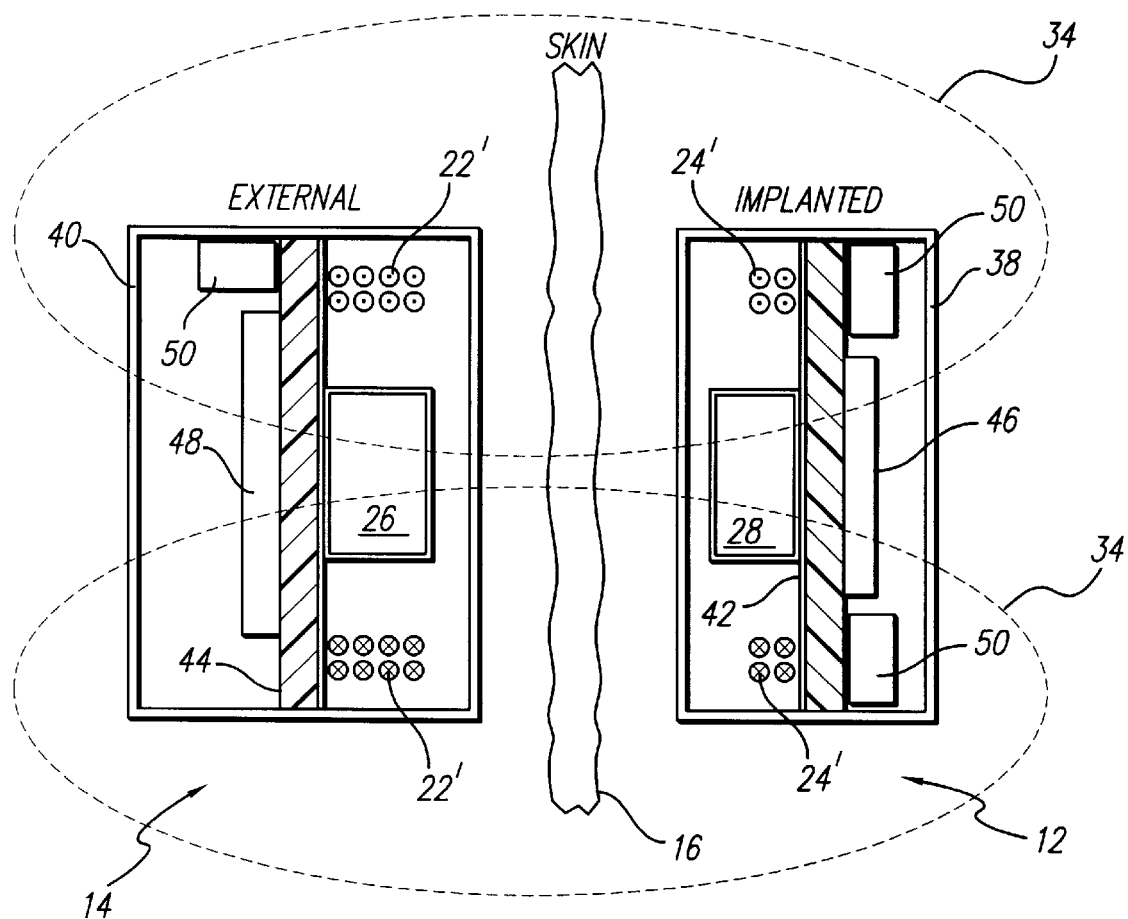
FIG. 3B schematically illustrates the implanted and external coils of FIG. 3A and further shows the use of a permanent magnet and/or keeper in order to hold the two coils a proper aligned relationship, and further illustrates other components that are typically used within an implanted device and an external device.

FIG. 3B schematically illustrates a preferred way for packaging an implant device 12 and external device 14. The implant device 12 includes an implanted coil 24' (represented as having 4 turns) mounted within an implant housing 38. The external device similarly has an external coil 22' (represented as having 8 turns) mounted within an external housing 40. The implant coil 24' of the implant device 12 is mounted on a suitable printed circuit (pc) board 42, or other substrate, held within the housing 38. The magnetic element 28 is also mounted on the pc board 42, centered within the coil 24'. Other circuit elements, e.g., an integrated circuit (IC) processor 46, and electrical components 50, such as capacitors, resistors, and the like, are also mounted on the pc board. Similarly, the external coil 22' of the external device 14 is mounted on a suitable pc board 44, or other substrate, held within the external housing 40. The magnetic element 26 is also mounted on the pc board 44, centered within the coil 22'. Other circuit elements, e.g., an IC processor/controller 48, and electrical components 50, such as capacitors, resistors, and the like, are also mounted on the pc board. The magnetic field created by the current I1 flowing through the coils 22' is represented by the dotted lines 34.

The implant housing 38 must be made from a suitable biocompatible material, e.g., glass or ceramic or other material that allows a magnetic field to readily pass therethrough (so that inductive coupling is not hampered). The external housing 40 may be made from any suitable material, e.g., plastic, that does not interfere with inductive coupling. A suitable housing for use with the implant device 12 is described in U.S. Pat. No. 4,991,582, incorporated herein by reference.

Figure 4:
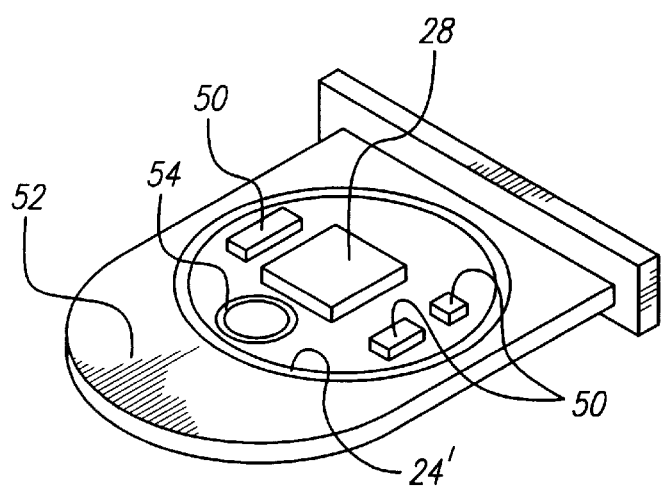
FIG. 4 is a perspective view of a circuit board on which a coil and magnet are mounted, along with other circuit components, for use within an ICS.

FIG. 4 shows a perspective view of a circuit board 52 on which an implant coil 24' and magnet 28 are mounted, along with other circuit components 50 for use within an ICS. The assembly shown in FIG. 4 also includes a smaller transmit coil 54 for allowing signals to be transmitted from the implant device 12 to an external device 14. The assembly shown in FIG. 4 is adapted to be inserted into a housing of the type described in the referenced '582 U.S. patent.

As should be evident from the foregoing, the typical implant medical device 12 employs a magnet, or magnetic element 28, positioned near or within an implant coil 24'. Magnetic flux, which represents the medium or vehicle by which power is transferred into the implant device, passes through the magnetic element 28.

As is known from physics, every electrical current has a magnetic field associated therewith. Similarly, every varying magnetic field, or varying magnetic flux, induces a current or voltage when a conductive medium is present. For purposes of the present invention, a desired current is inducted in the implant coil 22'. However, the magnetic element 28 also represents a conductive medium within the magnetic field in which an undesired current is induced. The undesired current induced in the magnetic element 28, for purposes of this application, is referred to as an "eddy" current, and such eddy current flows in a direction that is transverse to the direction of the magnetic flux. Such eddy current is dissipated in the resistance associated with the conductive medium. The power represented by the current dissipated in the resistance may be expressed as $[I(e)]^2 R$, where I(e) is the magnitude of the eddy current and R is the resistance of the conductive medium in which the eddy current is dissipated. The power thus dissipated is manifest as heat, and represents an energy loss.

In order to make the transfer of energy into the implant device more efficient, it is thus an object of the present invention to minimize the lost energy associated with the formation of eddy currents. This may be done by decreasing the resistance of the conductive medium wherein the eddy currents flow, and/or by minimizing the amplitude of the eddy currents formed. Of these two energy-loss-reduction techniques, decreasing the amplitude of the eddy currents is the most effective because the energy dissipated varies as the square of the eddy current amplitude.

In accordance with the present invention, the amplitude of the eddy currents formed in the conductive medium used for the implant magnetic element 28, and/or the external magnetic element 26, is achieved by creating high resistance barriers to eddy current flow, thereby minimizing the amplitude of any eddy currents that are formed. Such high resistance barriers, in turn, are created by sectionalizing or laminating the magnets or magnetic elements which are used.

Figures 5A, 5B:
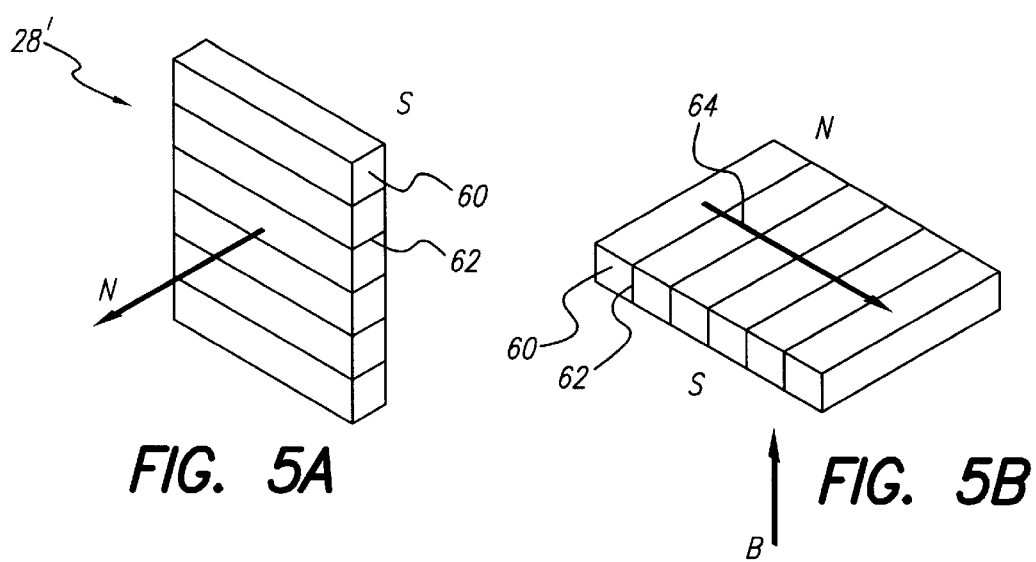
FIG. 5A shows a front view of a rectangular-shaped sectionalized magnet.
FIG. 5B shows a side view of the sectionalized magnet of FIG. 5A.

For example, with reference to FIG. 5A, there is shown a front view of a rectangular-shaped sectionalized magnet 28' made in accordance with the teachings of the present invention. FIG. 5B shows a side view of the sectionalized magnet 28' of FIG. 5A. As seen in FIGS. 5A and 5B, the sectionalized magnet is made from individual magnetic elements 60, having a rectangular or square cross section, and having one side polarized as a north pole and one sized polarized as a south pole. A multiplicity of such elements 60 are bonded together, using a suitable dielectric bonding agent, such as epoxy, so as to create a rectangular-shaped magnet 28', one face of which is a south pole, and the other face of which is a north pole. Thus, a dielectric boundary layer 62 is created between each of the sections 60. This dielectric boundary layer 62 represents a high resistance barrier to any eddy currents which might otherwise flow within the magnetic elements in the direction of the arrow 64 (FIG. 5B).

Figures 6A, 6B:
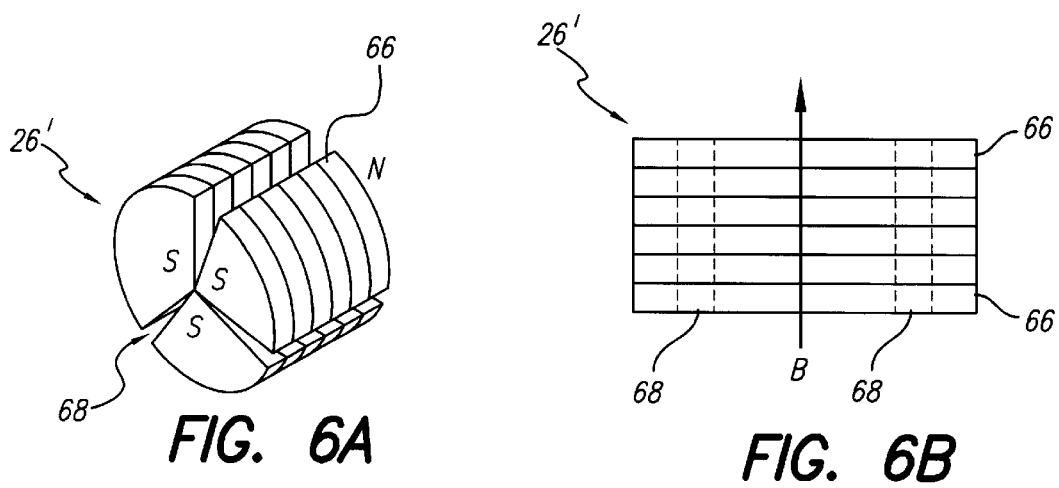
FIG. 6A illustrates one embodiment of a sectionalized cylindrical magnet.
FIG. 6B is a side view of the sectionalized cylindrical magnet of FIG. 6A.

FIG. 6A illustrates one embodiment of a sectionalized cylindrical magnet 26', which is the preferred shape of the magnet within the external device 14. It is to be noted, however, that a rectangular shaped magnet could also be used within the external device 14, if desired. The shape of the magnet is not important. What is important is that the magnet be sectionalized in a way so that a high resistance barrier is created which minimizes the amplitude of any eddy currents within the magnetic material.

FIG. 6B is a side view of the sectionalized cylindrical magnet of FIG. 6A. Note from these figures that the cylindrical magnet is sectionalized into thin slices 66. Wedge-shaped openings 68 may optionally be made in each slice at desired locations in each slice. Although shown in FIG. 6B as being wedge-shaped, such openings may in practice comprise a narrow slot. These wedge- or other-shaped openings are filled with a suitable dielectric (insulative) material, thereby providing a high resistance barrier to any eddy currents that might tend to flow around or near the periphery of the slice. The dielectric material also serves as a bonding agent or cement that glues the slices together to form the sectionalized magnet.

It is noted that the wedge-shaped openings are optional and need not always be employed. That is, for many applications, simply using stacked layers, slices or segments to form the cylindrical magnet will be sufficient to keep eddy current losses at a minimum. Further, it is also possible to utilize a coiled (spiraling) lamination for the cylindrical magnet so long as the ends of the coil or spiral are not electrically connected to each other.

Figure 7:
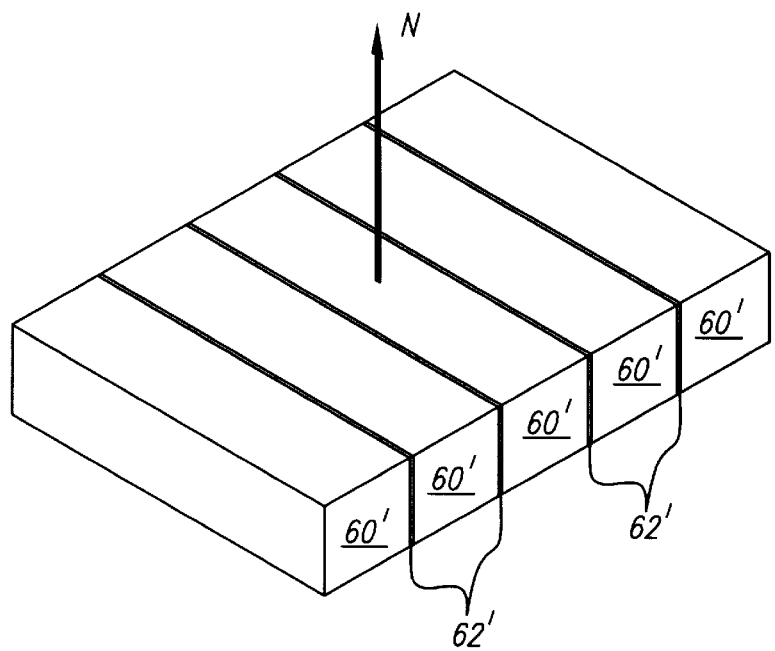
FIG. 7 shows a perspective view of another embodiment of a rectangular magnet that may be used within an ICS.

FIG. 7 shows a perspective view of another embodiment of a rectangular magnet that is preferably used within an implantable cochlear stimulator (ICS) (12) or within a headpiece (14) used with the ICS. Such sectionalized magnet is made up of five individual magnetic elements or sections 60', each of which is bonded to an adjoining section by way of a suitable bonding agent or cement that forms a dielectric layer 62'. The dielectric layer 62' provides a very high resistance barrier that minimizes eddy current formation. Each section 60' has approximate dimensions of 0.070 by 0.070 by 0.350 inches, which means the assembled sectionalized magnet has approximate dimensions of 0.070 by 0.350 by 0.352 inches, where the additional 0.002 inches represents the approximate combined thickness of the dielectric bonding agent. Any suitable dielectric cement or epoxy may be used to bond the magnetic sections together. A representative epoxy is "MD20", available from Master Bond, Inc., of Hackensack, N.J.

A five-piece sectionalized magnet as shown in FIG. 7, when used in an ICS system, results in a significant energy loss reduction. For example, tests conducted to date with the five-piece magnet shown in FIG. 7, have increased coil Q (quality factor) from 22 to 30 at 200 KHz. Although these results (obtained using the five-piece magnet shown in FIG. 7) are somewhat dependant upon the load connected to the inductive coupled coils, the tests conducted indicate that the overall power transfer losses are reduced by approximately 20%.

Figure 8:
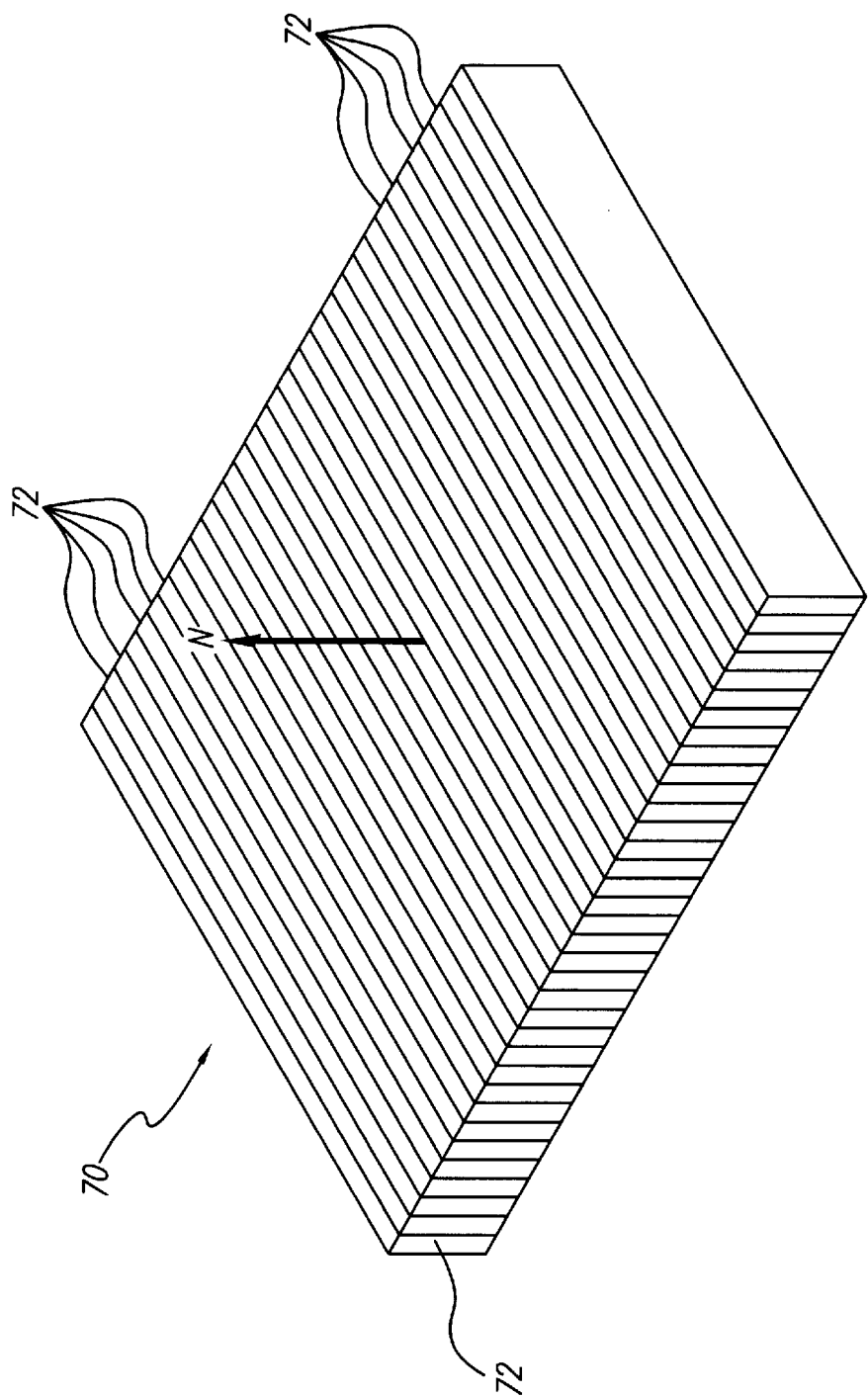
FIG. 8 depicts a perspective view of a rectangular-shaped laminated keeper that may be used within an ICS in accordance with a preferred embodiment of the invention.

FIG. 8 depicts a perspective view of a rectangular-shaped laminated magnetic keeper 70 that may be used within an ICS in accordance with a preferred embodiment of the invention. A magnetic keeper provides a low reluctance path for the magnetic flux, but is not itself a magnet, and resists being permanently magnetized. Thus, the magnetic keeper 70 provides an ideal element 28" for use within an implant device 12 where MRI may someday be needed. The particular magnetic keeper embodiment illustrated in FIG. 8 is intended for use within an ICS. As seen in FIG. 8, the keeper 70 utilizes thirty-five individual layers 72 that are laminated together using a suitable insulative bonding agent or cement. While the overall dimensions of the magnetic keeper 70 may be suited for a particular application, for an exemplary ICS application, the dimensions maybe, e.g., 0.350 by 0.355 by 0.070 inches. Thus, each individual segment or layer has dimensions that are approximately 0.350 inches long by 0.070 inches high by 0.010 inches thick.

The individual laminated layers of the keeper 70 may be made from any suitable material. Preferred materials include silicon steel or Hiperco Alloy 50. Silicon steel is a common material that is commercially available from numerous sources. Hiperco Alloy 50 may be obtained from Carpenter Technology Corporation, a Division of Carpenter Steel Company, of Auburn, Calif.

Figure 9A:
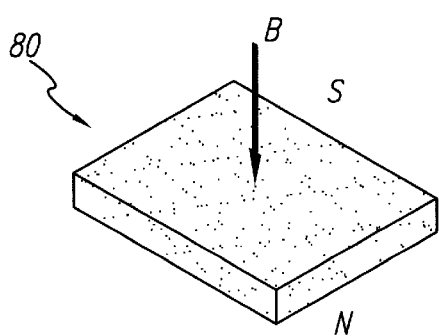
FIG. 9A illustrates another embodiment of a particle-based magnet which is sintered with a dielectric.
Figure 9B:
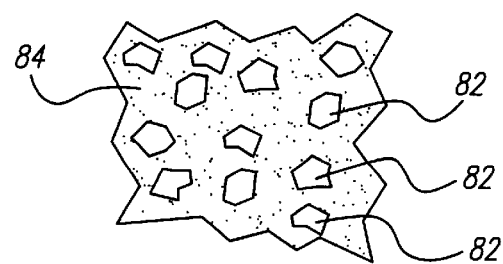
FIG. 9B shows an enlarged view of a portion of the magnet of FIG. 9A, and illustrates the particles and dielectric.

FIG. 9A illustrates another embodiment of a particle-based magnet that may be used with the invention. The particle-based magnet 80 is made from many magnetic particles 82 which are electrically-isolated from each other. The particles 82 are typically sintered and shaped, as desired, and immersed or embedded within a dielectric 84. FIG. 9B shows an enlarged view of a portion of the magnet 80 of FIG. 9A, and schematically illustrates the particles 82 and dielectric 84. During the sintering process, the individual magnetic particles 82 are subjected to a external magnetic field in order to align such particles in a desired polarity. Further details associated with such a particle-based magnet may be found in U.S. Pat. No. 5,594,186, entitled "High Density Metal Components Manufactured by Powder Metallurgy", incorporated herein by reference. Commercially, such a particle-based magnet 70 may be made from a material known as "Accucore", available from Magnetics International, Inc., of Burns Harbor, Ind.

As described above, it is thus seen that the present invention provides an implant system that efficiently transfers signals and power between an external portion and an implanted portion. That is, it is seen that the invention provides an implant device that reduces the amount of energy lost to the magnet or keeper, thereby increasing the efficiency of the implant device.

As further described above, it is seen that the invention provides an implantable cochlear stimulator (ICS) system having sectionalized or laminated magnets and/or keepers in an external portion and in an implantable portion, wherein such magnets and/or keepers are used to hold the external portion in proper alignment with the implant portion when the ICS system is in use, and wherein the sectionalized or laminated magnets and/or keepers reduce the amount of energy lost in the magnets or keepers, thereby making energy transfer between the two components more efficient.

While the invention herein disclosed has been described by means of specific embodiments and applications thereof, numerous modifications and variations could be made thereto by those skilled in the art without departing from the scope of the invention set forth in the claims.

What is claimed is:

1. An implantable medical device comprising:
   a receiving coil adapted to be electromagnetically coupled with a transmitting coil of an external device;
   a magnetic element responsive to a magnetic field for holding the implantable medical device in a desired position that aligns the receiving coil with the transmitting coil for efficient power and signal transfer between the receiving and transmitting coils;
   means for reducing energy loss within the magnetic element as power and signal transfers occur between the receiving and transmitting coils;
   whereby the implantable medical device operates with less loss relative to the amount of energy coupled into the receiving coil.

2. The implantable medical device of claim 1 wherein the magnetic element comprises a permanent magnet, and wherein the means for reducing energy loss within the permanent magnet comprises magnetic sections joined together with a dielectric (electrical insulative) material.

3. The implantable medical device of claim 1 wherein the magnetic element comprises a magnetic keeper made from a magnetic material that reduces magnetic reluctance.

4. The implantable medical device of claim 3 wherein the means for reducing energy loss within the magnetic keeper comprises discrete sections of the magnetic keeper joined together with a dielectric (electrical insulative) glue or cement, whereby the magnetic keeper comprises a sectionalized magnetic keeper.

5. The implantable medical device of claim 3 wherein the means for reducing energy loss within the magnetic keeper comprises laminations of the magnetic material joined together with a dielectric (electrical insulative) glue or cement, whereby the magnetic keeper comprises a laminated magnetic keeper.

6. The implantable medical device of claim 3 wherein the means for reducing energy loss within the magnetic keeper comprises making the magnetic material from magnetic particles sintered with a dielectric material between the particles.

7. The implantable medical device of claim 3 wherein the magnetic material from which the magnetic keeper is made is selected from the group of magnetic materials comprising: silicon steel, Hiperco Alloy 50, and Accucore.

8. An improved implantable medical device having a receiving coil adapted to be coupled with an external magnetic field for providing power and control signals to the implantable medical device, and further including a magnetic element that helps align the receiving coil with the external magnetic field in order to make the transfer of power and control signals more efficient, wherein the improvement comprises a magnetic element having laminations, sections or particles that minimize the formation of eddy currents in the magnetic element in the presence of a magnetic field.

9. The improved implantable medical device of claim 8 wherein the medical device comprises an implantable cochlear stimulator (ICS), and further wherein the magnetic element comprises a magnetic keeper made from a material that provides a low magnetic reluctance path for magnetic flux, but which does not become permanently magnetized in the presence of a strong externally-generated magnetic field, such as one produced by a magnetic resonance imaging (MRI) system.

10. The improved implantable medical device of claim 9 wherein the magnetic material from which the magnetic keeper is made is selected from the group of magnetic materials comprising: silicon steel, Hiperco Alloy 50, and Accucore.

11. A medical device system comprising a first part and a second (non-implanted) part, the first part and the second part each having a coil therein through which power may be inductively coupled from the first part to the second part when the respective coils are aligned, comprising:

a first magnetic element in the first part;

a second magnetic element in the second part adapted to be magnetically attracted to the first magnetic element in the first part, which attraction aligns the respective coils for efficient power and signal transfer;

wherein at least the second magnetic element has electrical resistance blocking means therein for minimizing the formation of eddy currents in the second magnetic element when in the presence of a magnetic field, thereby making the transfer of power into the second part more efficient.

12. The medical device system of claim 11 wherein the second magnetic element comprises a sectionalized magnetic keeper made from discrete sections of a magnetic material that provides a low reluctance path for the magnetic field, wherein the discrete sections are bonded together with a dielectric material exhibiting a high electrical resistance.

13. The medical device system of claim 11 wherein the second magnetic element comprises a laminated magnetic keeper made from discrete layers of a magnetic material that provides a low reluctance path for the magnetic field, wherein the discrete layers are held together with a dielectric material exhibiting a high electrical resistance.

14. The medical device system of claim 11 wherein the second magnetic element comprises electrically-isolated magnetic particles.

15. The medical device system of claim 14 wherein the second magnetic element comprises a sintered magnetic keeper made from magnetic particles sintered with a dielectric material between the particles, wherein the particles provide a low reluctance path for the magnetic field, and wherein the dielectric material exhibits a high electrical resistance.

16. A method for reducing power losses associated with the transfer of energy into an implantable medical device from an external device via inductive coupling, the implantable medical device having a first magnetic element therein adapted to be magnetically attracted to a second (non-implanted) magnetic element, comprising:

positioning the first magnetic element relative to an implanted coil within the implantable medical device so that when the first magnetic element is maximally magnetically attracted to the second magnetic element, the implanted coil is aligned with an external coil for efficient inductive coupling; and configuring the first (implanted) magnetic element so as to minimize the formation of eddy currents therein when the second magnetic element is in the presence of a magnetic field.

17. The method of claim 16 wherein configuring the first magnetic element to minimize eddy current formation comprises sectionalizing the first (implanted) magnetic element by separating the magnetic element into discrete sections and bonding the sections together with a dielectric material.

18. The method of claim 16 wherein configuring the first magnetic element to minimize eddy current formation comprises laminating the first (implanted) magnetic element by forming the element from discrete layers and bonding the layers together with a dielectric material.

19. The method of claim 16 wherein configuring the first magnetic element to minimize eddy current formation comprises sintering the first (implanted) magnetic element by forming the element from discrete magnetic particles and sintering a dielectric material between the particles.

20. The method of claim 16 further including configuring the second (non-implanted) magnetic element so as to minimize the formation of eddy currents therein when the second magnetic element is in the presence of a magnetic field.

* * * * *